United States Patent
Varghese et al.

(10) Patent No.: US 7,632,230 B2
(45) Date of Patent: Dec. 15, 2009

(54) HIGH RESOLUTION ELASTOGRAPHY USING TWO STEP STRAIN ESTIMATION

(75) Inventors: Tomy Varghese, Madison, WI (US); Hairong Shi, Madison, WI (US); Hao Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 513 days.

(21) Appl. No.: 11/384,607

(22) Filed: Mar. 20, 2006

(65) Prior Publication Data

US 2007/0083113 A1    Apr. 12, 2007

Related U.S. Application Data

(60) Provisional application No. 60/725,475, filed on Oct. 11, 2005.

(51) Int. Cl.
*A61B 8/00* (2006.01)
(52) U.S. Cl. .............. 600/437; 600/444; 600/443; 600/439; 600/438; 600/446; 600/407; 73/597
(58) Field of Classification Search ............ 600/437, 600/443, 444, 438, 439
See application file for complete search history.

(56) References Cited

U.S. PATENT DOCUMENTS 5,474,070 A    12/1995   Ophir et al.
6,066,095 A *   5/2000   Morsy et al. ............... 600/438
6,277,074 B1 *  8/2001   Chaturvedi et al. ......... 600/437
6,508,768 B1    1/2003   Hall et al.
7,223,241 B2 *  5/2007   Radulescu ................. 600/443

OTHER PUBLICATIONS

Pawan Chaturvedi, 2-D Companding For Noise Reduction In Strain Imaging, IEEE Transactions on Ultrasonics, Ferroelectrics, and Frequency Control, vol. 45, No. 1, Jan. 1998, pp. 179-191.

S Kaisar Alam, An Addaptive Strain Estimator for Elastography, IEEE Transactions on Ultrasonics, Ferroelectrics, and Frequency Control, vol. 45, No. 2, Mar. 1998, pp. 461-472.

International Search Report for International Application No. PCT/US2006/037581.

\* cited by examiner

*Primary Examiner*—Long V Le
*Assistant Examiner*—Nigel Fontenot
(74) *Attorney, Agent, or Firm*—Boyle Fredrickson, S.C.

(57) ABSTRACT

High-resolution elastography employs a multiple-step process in which successively finer samplings of data and smaller areas of data are evaluated to provide increasingly accurate displacement measurements, wherein each displacement measurement guides the determination of corresponding regions of comparison used in the next displacement evaluation.

26 Claims, 5 Drawing Sheets

HIGH RESOLUTION ELASTOGRAPHY USING TWO STEP STRAIN ESTIMATION

CROSS-REFERENCE TO RELATED APPLICATIONS

This application is based on provisional application 60/725,475 filed Oct. 11, 2005, and entitled "Two-Step Strain Estimation in Elastography.

STATEMENT REGARDING FEDERALLY SPONSORED RESEARCH OR DEVELOPMENT

This invention was made with United States government support awarded by the following agencies:
NIH Grant R21 EB003853.
The United States has certain rights in this invention.

BACKGROUND OF THE INVENTION

The present invention relates to ultrasonic imaging and in particular to an apparatus and method for making ultrasonic elastography measurements.

Elastography is an imaging modality that reveals the stiffness properties of tissue, for example, axial strain, lateral strain, Poisson's ratio, Young's modulus and other common strain and strain-related measurements. In elastography, strain measurements may be collected over an area and compiled as a two-dimensional array of data which may be mapped to a grey or color scale to form a strain "image." Analogously, strain measurements may be collected over a volume displayed either three-dimensionally or as a series of stacked two-dimensional images.

In quasi-static elastography, two images of tissue ("pre-compression" and "post-compression") are obtained by the ultrasound device with the tissue in two different states of compression, for example, no compression and a given positive or negative (tensile) compression. The tissue may be compressed by an external agency such as a probe or the like, or muscular action or movement of organs near the tissue. Strain may be deduced from these two images by computing gradients of the relative local shifts or displacement in the images along the compression axis. Quasi-static elastography is analogous to a physician's palpation of tissue in which the physician identifies firm structures by pressing the tissue and detecting the amount the tissue yields under this pressure.

Determining the relative displacement of the tissue between the two compression images is normally done by analyzing successive portions of the ultrasonic signal in a series of discrete 1-D windows or 2-D or 3-D kernels. The windows define portions of the ultrasonic signal at successive times representing reflections from tissue at successive locations along the path of the ultrasound. Kernels denote 2-D or 3-D search regions in the 2-D or 3-D received ultrasound echo signals in the B-mode or RF data. The ultrasonic signal may be either an envelope of the amplitude of a received ultrasonic echo or the echo signal (RF) itself.

Generally, the signal in each window in the pre-compression image is cross-correlated to the signal in a search area of the post-compression image to find corresponding window in the post-compression data and thereby determine slight shifts between the signals and thus shifts in location of the underlying tissue with compression. This cross-correlation process is repeated for successive windows of the ultrasonic signal yielding local displacement of tissue for each window. The gradient of these local displacements yields a measure of the local strains in the tissue.

The resolution of elastography is fundamentally limited by the size of the windows used to determine the displacement of the tissue. Currently, larger windows are used, for example, on the order of twenty wavelengths (a centimeter or more at common ultrasound frequencies), too large to effectively image extremely smaller objects such as the calcifications that accompany breast cancer.

Smaller window sizes, for example, on the order of one wavelength (less than a millimeter at common ultrasound frequencies), potentially provide an increase in the resolution of elastography, but are practically limited by problems of tissue displacement moving the echo signals that arise from this tissue to be entirely out of the window and increased statistical miscorrelation as the amount of correlated data is reduced and the discipline of only correlating within corresponding windows is relaxed.

The problem of post-compressed tissue failing to remain within corresponding windows of the post-compressed tissue can be addressed by using larger size windows for the post-compression data or by temporal stretching of the post-compression data to improve the alignment of the tissue between windows. This latter approach tends to introduce artifacts into the post-compression data where some regions are over stretched while other regions are under stretched. The former approach still faces the problem of statistical mismatching in the cross correlation process promoted by the unmatched window sizes.

SUMMARY OF THE INVENTION

The present invention provides a high-resolution ultrasonic elastography machine using window sizes less than two wavelengths (on the order less than a millimeter) for common ultrasound frequencies. The above-described problems of small window sizes are avoided with a multi-step correlation process starting with large windows which provide a coarse estimation of tissue displacement. This coarse estimation is then used to guide the placement of successively smaller windows in later steps of the process, the displacement at each window size guiding the placement of the next smaller windows. As so guided, the successively smaller windows may be placed on corresponding echo signals, eliminating the problem of tissue movement outside of the windows and significantly reducing the risk of miscorrelation.

Specifically then, the present invention provides high resolution ultrasonic elastography in which pre-compression and post-compression ultrasonic data sets are collected, and a first comparison is made of the pre-compression and post-compression data at a plurality of corresponding first pre-compression region and first post-compression regions to determine a coarse-displacement of material of the imaged object resulting from compression. The determined coarse-displacements are then used to identify second post-compression regions corresponding to a plurality of second pre-compression regions within each first pre-compression region and a second comparison is made of the pre-compression and post-compression data within the plurality of second pre-compression regions corresponding second post-compression regions to determine a finer-displacement of material of the imaged object resulting from compression. An elastographic image based on the finer displacement is then output.

Thus, it is an object of at least one embodiment of the invention to obtain the benefits of a large window or kernel size in accommodating tissue displacement and the benefits of a small window or kernel size for high-resolution imaging. The large window or kernel sizes provide a coarse-displacement map which guides the small window comparisons.

The data of the first pre-compression regions and first post-compression regions are down-sampled to reduce the number of data samples that otherwise would need to be compared.

Thus it is another object of at least one embodiment of the invention to provide an efficient multistep/multiregion process where the amount of data is limited to be commensurate with the precision of the necessary displacement determination.

The first comparison compares amplitude envelopes of the ultrasonic data sets and the second comparison compares ultrasonic data underlying the amplitude envelopes.

Thus it is another object of at least one embodiment of the invention to provide a simple compression system (envelope extraction) that is resistant to aliasing that can occur with standard down-sampling.

The method may further include the steps using the determined finer-displacements to identify third post-compression regions corresponding to a plurality of third pre-compression regions within each second pre-compression region and making a third comparison of the pre-compression and post-compression data within the plurality of third pre-compression regions and corresponding third post-compression regions to determine an even finer displacement of material of the imaged object resulting from compression.

Thus, it is an object of the invention to provide an arbitrary number of steps of displacement refinement allowing extremely fine resolution to be obtained even when assumptions about continuity in the displacement field are invalid, such as when imaging blood vessels that are compressed or expanded under pulsatile blood flow.

The first comparison may compare portions of the ultrasonic data sets having no less than ten wavelengths of data while the second comparison may compare portions having less than ten wavelengths of data and preferably less than two wavelengths of data.

Thus, it is an object of the invention to significantly increase the resolution of ultrasonic elastography.

The first comparison may produce a set of displacement values as a function of depth along an ultrasonic axis through the imaged object and may include the step of interpolating between the displacement values to produce the coarse-displacement.

Thus, it is an object of the invention to provide extremely fast displacement mapping commensurate with the purpose of providing guidance for the smaller windows while minimizing any time penalty for two steps of comparison.

The coarse-displacement data set may be filtered before its use in guiding the placement of the smaller comparison windows.

Thus, it is another object of the invention to make use of a priori knowledge about properties of the imaged material, for instance, tissue, to improve the coarse-displacement data, for example, through low pass filtering or elimination of statistical anomalies.

The pre-compression and post-compression ultrasonic data may be RF data.

Thus, it is an object of the invention to provide a system that may take full advantage of single-wavelength features of the RF data.

The ultrasonic data may be acquired along the axis of compression or across the axis of compression and may be used to form a two-dimensional or three-dimensional image from multiple such ultrasonic data acquired in a linear, curvilinear or angular fashion.

Thus, it is another object of the invention to provide for a strain mapping technique that is applicable to a wide variety of ultrasonic strain determination applications.

These particular objects and advantages may apply to only some embodiments falling within the claims, and thus do not define the scope of the invention.

DETAILED DESCRIPTION OF THE PREFERRED EMBODIMENT

Figure 1:
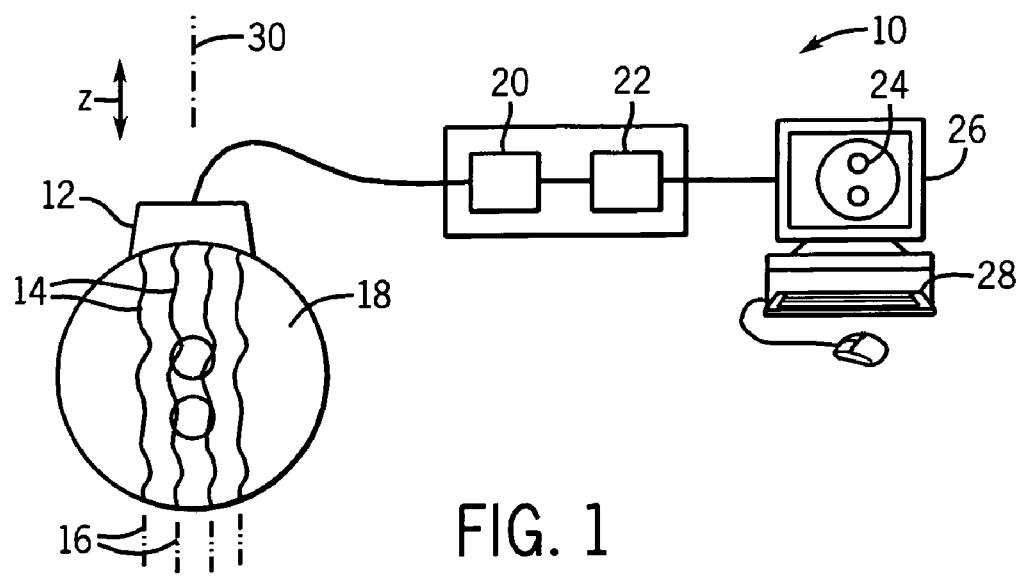
FIG. 1 is a simplified block diagram of an ultrasound-imaging machine such as may be used for elastography per the present two-step invention.

Referring now to FIG. 1, an ultrasonic imaging system 10 may provide an ultrasound transducer 12 producing and receiving ultrasonic echo signals 14 along multiple ray paths 16 through an imaged object such as tissue 18 of the patient. For the purpose of illustration, the received the ultrasonic echo signals 14 are shown superimposed on the tissue 18 to depict the relationship between these time domain signals to reflections of ultrasonic energy from various points along the ray paths 16.

The ultrasonic echo signals 14 may be received and processed by ultrasound acquisition circuitry 20 of a type well known in the art to provide radio frequency data to an elastography processor 22. A suitable ultrasonic imaging system 10 for the present invention may use 7.5-megahertz frequency with a transducer having five-hundred and twelve or more consecutive elements to provide for ultrasound beams generated with an aperture of sixty-four element beams of ultrasonic echo signal 14.

Generally, as will be described in more detail below, the elastography processor 22 produces elastographic images 24 that may be displayed on a display terminal 26 communicating with the elastography processor 22. The elastographic images 24 may provide for a visual representation of one or more measures of stiffness of the tissue 18 of the patient. An input device 28 may communicate with the elastography processor 22 to allow the user to set or change various processing parameters used by the ultrasound acquisition circuitry 20 or the elastography processor 22.

Figure 2:
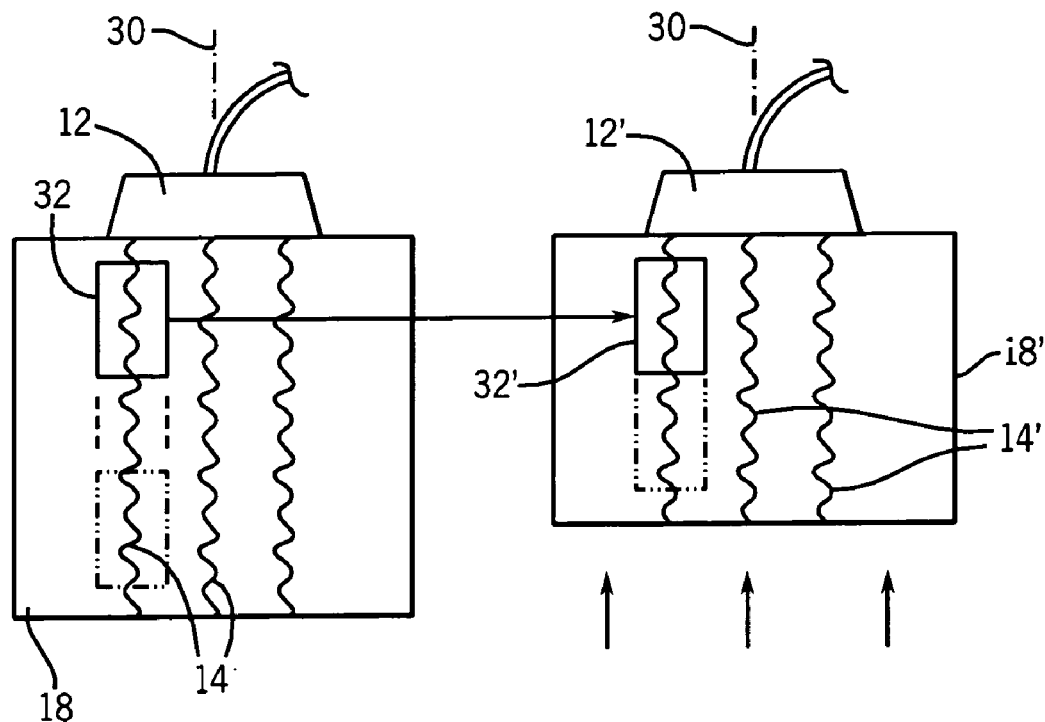
FIG. 2 is a diagram showing the first step of the invention in which corresponding large windows of signals from pre-compressed and post-compressed tissue are compared to obtain a coarse determination of tissue displacement.
Figure 6:
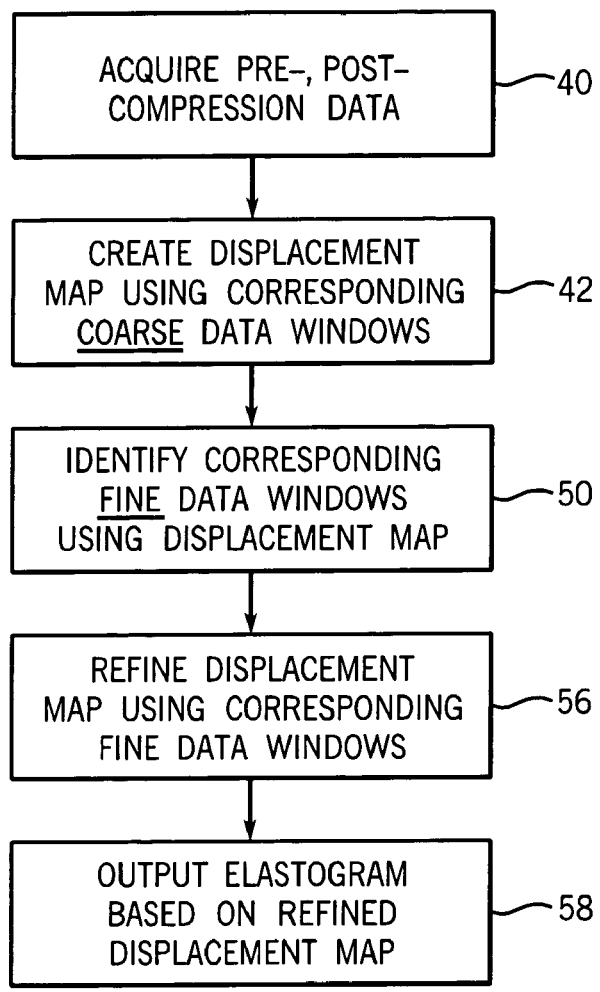
FIG. 6 is a flow chart depicting the steps of FIGS. 2 through 5.

Referring now to FIGS. 1, 2, and 6, during a first step in an elastographic acquisition using the above-described ultrasonic imaging system 10 as indicated by process block 40 of FIG. 6, the tissue 18 of the patient may be compressed along a compression axis 30 typically, but not necessarily, aligned with the ray paths 16. For this purpose, the ultrasonic imaging system 10 may include a separate compressor (not shown) or the compression may be incidental to muscle or organ movement, or performed manually by pressing down on the transducer 12 at an appropriate time. The compression is performed to allow the ultrasonic imaging system 10 to collect at least two sets of ultrasonic echo signals 14, each with the tissue 18 in a different state of compression, e.g., pre-compression and post-compression. For simplicity, in the following description and claims, the terms "pre-compression" and "post compression" refer simply to two different states of compression and not necessarily a relative order of acquisition or relative magnitude of compression. Typically, a compression of approximately one percent is sought. Larger compressions can also be tracked using two-dimensional cross-correlation processing.

Two-Step Processing

Referring to FIG. 2, the ultrasonic echo signals 14 acquired in pre-compressed tissue 18 may be compared to ultrasonic echo signals 14 post-compressed tissue 18' to deduce tissue movement or deformation caused by the compression. For this purpose, each ultrasonic echo signal 14 and 14' is divided into a set of time sequential coarse-scale kernels or windows 32 and 32', respectively, normally each greater than ten wavelengths of the ultrasonic echo signal 14 and preferably on the order of twenty wavelengths. As is understood in the art, a wavelength is the distance the ultrasonic echo signal 14 travels through the tissue 18 during one cycle of the ultrasound signals 14, and thus will vary depending on the frequency of the ultrasonic transducer 12.

The compression of the tissue 18 (depicted as tissue 18') will cause a shifting of relative portions of the ultrasound signals 14 between coarse-scale windows 32 and 32' caused by displacement of underlying tissue 18, 18'. That is, the ultrasonic echo signal 14 associated with a particular structure in the tissue 18 will be found in a different location in coarse-scale window 32 than in 32'. Ideally coarse-scale windows 32 and 32' are sized so that, with foreseeable compression of the tissue 18, a portion of the ultrasonic echo signal 14 in coarse-scale window 32 will still be within coarse-scale window 32' for conceivable compression amounts thus limiting the search area (e.g., the amount of relative shifting) that will be required of the coarse-scale window 32' necessary to find a location that provides good correlation with the data of the coarse-scale window 32.

As indicated by process block 42 of FIG. 6, for each of the coarse-scale windows 32 on ultrasonic echo signals 14, a cross correlation may be performed with the corresponding coarse-scale window 32' on the ultrasonic echo signal 14' as a function of movement of the location of the coarse-scale window 32'. The cross correlation provides a peak value that indicates a shift of tissue relative to window 32 during the compression reflected in the offset of the coarse scale windows 32 and 32' at maximum correlation. The amount of this shift provides data points 46 indicating tissue displacement ($\Delta z$) as a function of depth (z) along the ray path 16 and may be stored to produce a coarse-displacement map 44 for each ultrasonic echo signal 14. One data point 46 may be calculated for each coarse-scale window 32, and the separation between displacement points 46 is therefore a function of the size of coarse scale windows 32. In the preferred embodiment, each coarse-scale window 32 does not overlap the next window on a given ultrasonic echo signal 14 to speed processing because only a coarse-displacement map 44 is required.

The coarse-displacement map 44 may be further processed by interpolating between points 46 to provide a continuous function 48 and low pass filtering of that function according to a priori knowledge of tissue characteristics in smoothing displacement of post-compressed tissue. Other statistical measures may be taken to improve the coarse-displacement map 44 including, for example, curve fitting and the elimination of statistically outlying points caused by noise or other artifacts.

Figure 4:
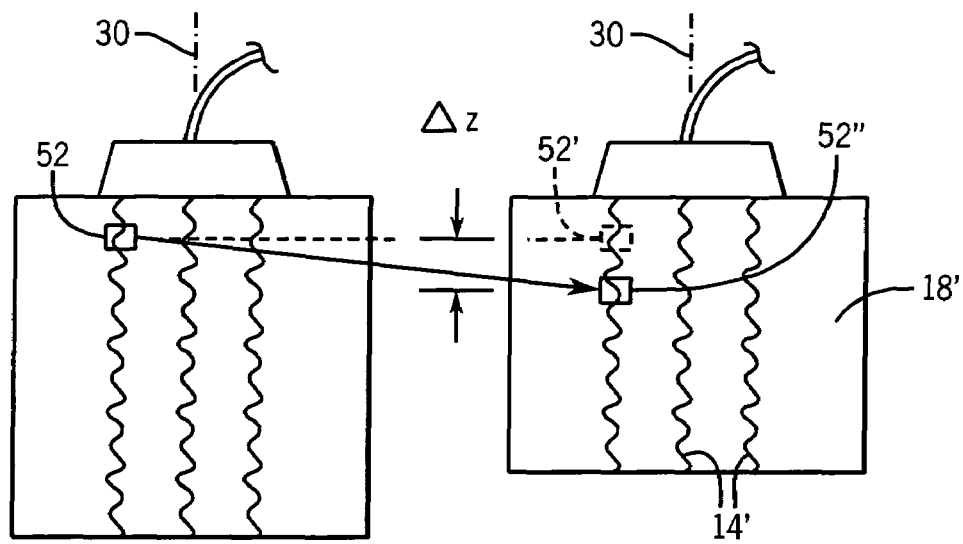
FIG. 4 is a figure similar to that of FIG. 2 showing a second step of the invention in which corresponding small windows of signals from pre-compressed and post-compressed tissue are compared to obtain a fine determination of tissue displacement; the corresponding small windows being identified by the coarse-displacement map of FIG. 3.
Figure 5:
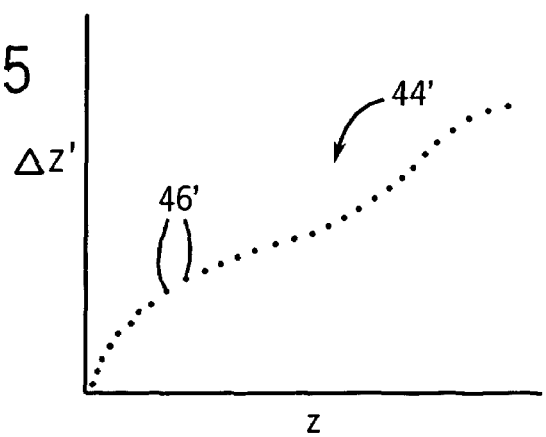
FIG. 5 is a figure similar to that of FIG. 3 showing a refinement of the coarse-displacement map of FIG. 3 using the measurements for the small windows of FIG. 4.

Referring now to FIG. 4 and process block 50 of FIG. 6, fine-scale windows 52 and 52' on each of ultrasonic echo signals 14 and 14', respectively, are less than ten wavelengths, preferably less than two wavelengths, and as little as a single wavelength of the ultrasonic echo signal 14 in length. The reduced size of each fine-scale window 52 and 52' significantly reduces the likelihood that tissue in a fine-scale window 52 in the pre-compressed tissue 18 will by chance contain the same tissue as that in fine-scale window 52' in the post-compressed tissue 18' at the same relative location. Further, the limited amount of data in the fine-scale window 52 increases the possibility of false correlations with unrelated portions of ultrasonic echo signal 14' should fine-scale window 52' be scanned over an arbitrarily large search area in making a correlation.

Figure 3:
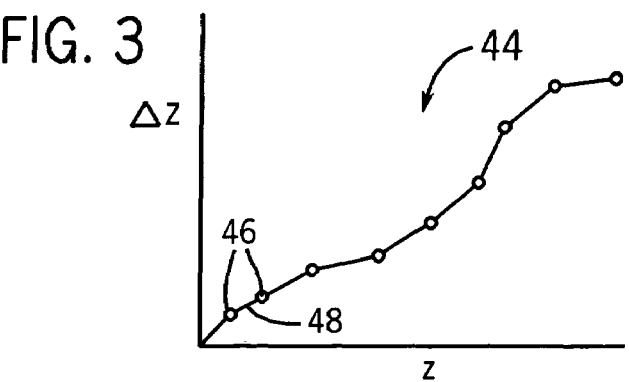
FIG. 3 is a graph showing a plot of the coarse-displacement determined in the first step of the invention for multiple corresponding large windows.

For these reasons, a new, displaced, fine-scale window 52" having the same dimensions as fine-scale window 52 is identified on ultrasonic echo signal 14' having a displacement from fine-scale window 52' derived from the coarse-displacement map 44 of FIG. 3. Specifically, for each fine-scale window 52, the z-location of the fine-scale window 52 is applied to the coarse-displacement map 44 to determine the likely tissue shift $\Delta z$ at that z-location, and thereby anticipate the likely location of fine-scale window 52" covering a portion of ultrasonic echo signals 14' from the same tissue as that producing the ultrasonic echo signal 14 covered by fine-scale window 52.

For each of the fine-scale windows 52 on ultrasonic echo signals 14, a cross correlation may be performed with the corresponding fine-scale window 52" on the ultrasonic echo signal 14' at various offsets in a limited range about this initial location of fine-scale window 52". The cross correlation, as before with windows 32 and 32', provides a peak value that indicates a shift of tissue relative to window 52 during the compression.

This cross-correlation process is repeated for each of a series of windows 52 as indicated by process block 56 to create a new fine-displacement map 44' from the cross correlations between corresponding fine-scale window 52 and 52". Fine-scale windows 52 may overlap slightly so as to provide data points 46' that may be more frequent than the width of the fine-scale window 52.

The fine-displacement map 44', as indicated by process block 58 of FIG. 6, may be used directly to create an elastographic image where stiffness is deduced by the slope of the curve of the fine-displacement map 44' according to methods well-known in the art. Additional processing, for example, filtering and statistical processing, may be optionally performed on fine displacement map 44' prior to reconstruction of the image.

Multistep (Pyramid) Processing

Figure 8:
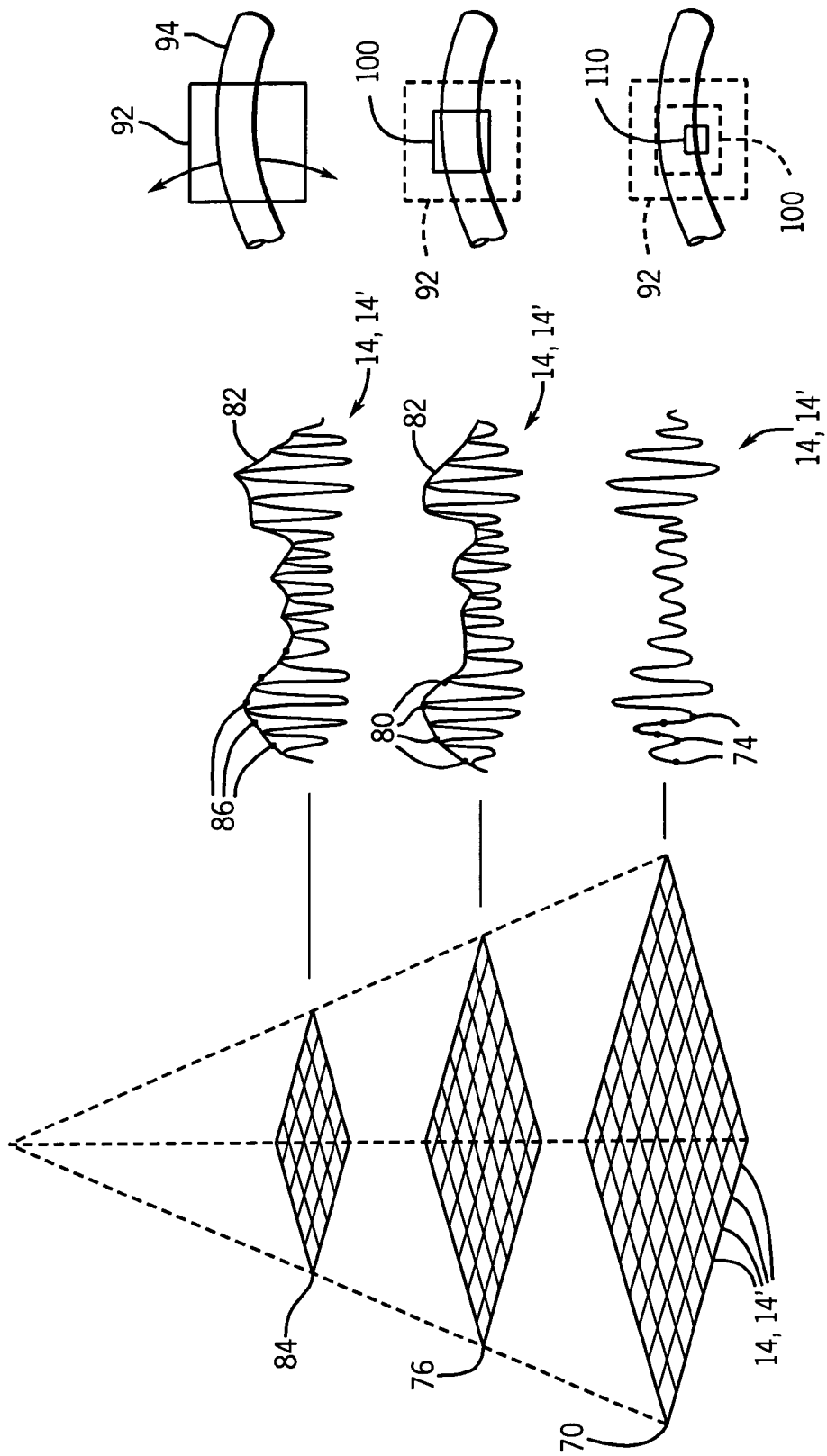
FIG. 8 is a representation of a pyramid, formed from the data of both of the pre-compression and post-compression ultrasound data, as successively compressed in a multi-step embodiment of the present invention, showing for each step of compression a matching depiction of a corresponding waveform and sampling, and a depiction of a relative window size.

Referring now to FIG. 8, the pre-compression ultrasonic echo signals 14 and post-compression ultrasonic echo signals 14' may be assembled into a radio-frequency data array 70 having successive rows incorporating digitized samples 74 of echo signals 14 or 14' from spatially adjacent tissue. While the data array 70 is shown as a two-dimensional array, it will be understood that it may alternatively be a three dimensional array of data representing data over three corresponding spatial dimensions in the tissue 18.

The radio-frequency data array 70 may be down-sampled to produce first down-sampled data set 76 providing fewer data points and thus generally fewer rows and columns. The down-sampling process may simply down-sampling of radio-frequency data array 70, e.g., by combining and interpolating between the samples 74 (in two or three dimensions) of radio-frequency data array 70 to produce the smaller set of samples for first down-sampled data set 76, or may, in the preferred embodiment, be samples 80 taken at a lower sample rate on amplitude envelope 82 of the echo signals 14 or 14' using well known amplitude demodulation techniques. The amplitude envelope 82, having inherently lower frequency than the waveform 72 eliminates problems that may occur if the sample rate of samples 80 is less than the Nyquist frequency, (e.g., less than twice the highest frequency of echo signals 14 or 14'). The interpolation or enveloping is preferably performed in two directions for two dimensional array 70 reducing the number of rows and columns of data in the first down-sampled data set 76 and in three dimension for a three-dimensional array 70.

Similarly, the first down-sampled data set 76 may be down-sampled to produce second down-sampled data set 84 by down sampling and interpolation or other compression processes providing even fewer data points from samples 86 at a yet lower rate, and thus generally fewer rows and columns.

As will be discussed further below, the successive down-sampling of the radio-frequency data array 70 as first down-sampled data set 76 and second down-sampled data set 84 allows for efficient correlation of successively larger kernel or windows 110, 100 and 92, respectively, at higher speeds. The kernels or windows 110, 100, and 92 can be two or three dimensional depending on the dimensions of the data array 70. The larger windows provide lower accuracy displacement measurements, but such measurements are suitable for the successive refinement of displacement measurements provided by the present invention. Note that the combination of down-sampling and larger window sizes allows each window to have, if desired, a comparable number of data points for different sampling resolutions.

Figure 9:
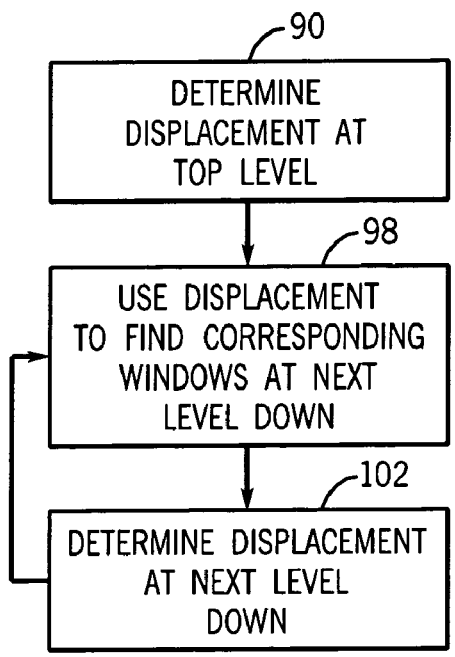
FIG. 9 is a flowchart showing the steps of the multi-step embodiment.
Figure 10:
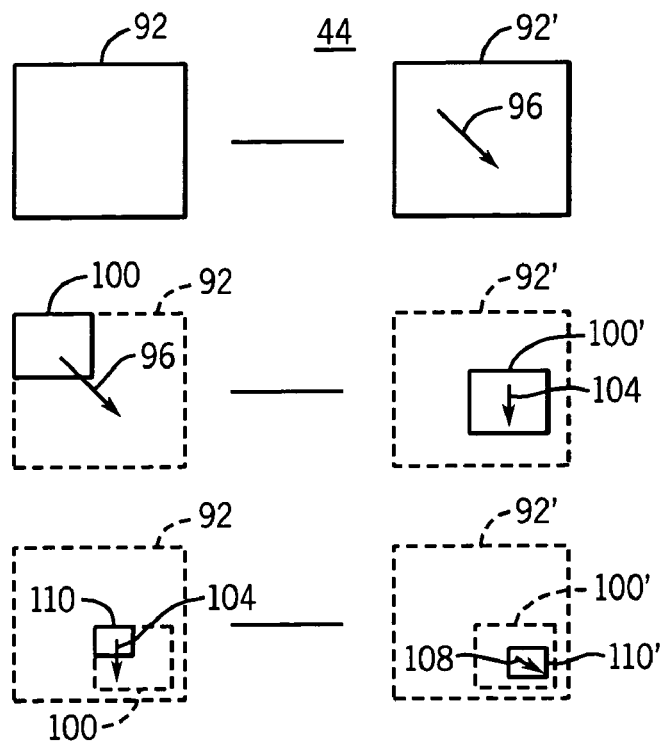
FIG. 10 is a set of figures similar to those of FIGS. 2 and 4 showing refinements of displacement vectors using successively smaller windows in the multi-step process.

Referring now to FIGS. 8, 9 and 10, at a first step indicated by process block 90 of this multi-step version of the invention, occurring after step 40 of FIG. 6, a displacement map 44' providing a series of displacement vectors 96 is created using the data of the second down-sampled data set 84 analyzed using a large window 92. The size of window 92 may, for example, be such as to fully cover a blood vessel 94, whose compression may be effected by the normal pulsatile flow of blood through the vessel 94. In this situation, the wall of the vessel 94 closest to the transducer (not shown) may move toward the transducer while the wall of the vessel 94 furthest from the transducer may move away from the transducer creating a non-monotonic displacement field normally unexpected in conventional displacement calculating algorithms. While the window 92 is relatively large, the down-sampling of the second down-sampled data set 84 means that the computational burden for cross correlation of the pre- and post-compression data of window 92 is well managed. The comparison of the data of the windows 92 and 92' maybe in two or three dimensions as would be appropriate for the data.

At process block 90, the pre-compression data of the second down-sampled data set 84 for each of a series of windows 92 is compared to the post-compression data of the second down-sampled data set 84 in corresponding windows 92' to determine a displacement vector 96 associated with each window 92, 92'.

At process block 98, a number of smaller windows 100 and 100' are then defined within each window 92 or a similar search area, as applied to the pre-compression and post-compression data, respectively, of the first down-sampled data set 76. Corresponding locations of windows 100 and 100' are determined using previously computed displacement vector 96 for the window 92 in which window 100 is located. Generally window 100' need not be in the same window 92 as window 100.

At process block 102 the comparison of these smaller corresponding windows 100 and 100' as the latter is scanned over a limited search area, is used to produce a new displacement map comprised of a set of displacement vectors 104 providing more accuracy than displacement vectors 96.

Process block 98 may then be repeated with yet smaller data window 110 being defined within each data window 100 applied to pre-compression data of the data set 70 and matched to a corresponding data window 110' in the post-compression data of the data set 70. At process block 102, a yet even more accurate displacement map may be constructed using displacement vectors 108 calculated from a comparison of the data of windows 110 and 110'. Data window 110 may be small enough that the assumptions about continuity or monotonicity of the displacement field apply.

At each level of this process, when displacement vectors 96, 104 and 108, are calculated, displacement vectors associated with low normalized cross-correlation coefficients may be replaced or interpolated from surrounding displacement vectors having higher normalized cross-correlation value. The threshold for such replacement may be empirically chosen.

In addition other filtering may be applied to the displacement vectors, for example, smoothing them with a cubic spline smoothing function.

Figure 7:
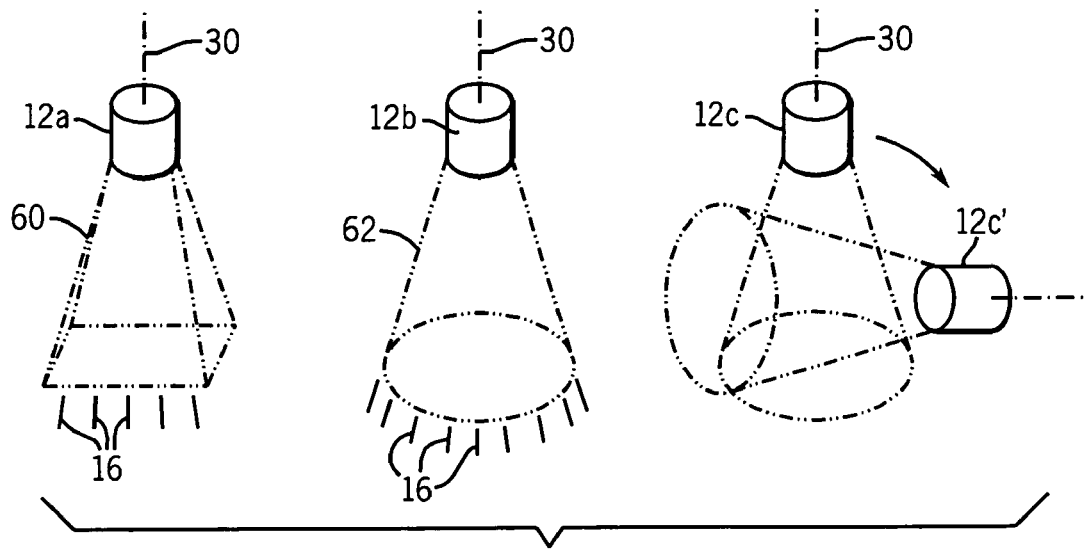
FIG. 7 is a simplified perspective view of several different modes of ultrasonic acquisition strategy to which the present invention may be applied.

Referring now to FIG. 7, the present invention is applicable to a wide variety of ultrasonic elastographic acquisitions where improved resolution is required including a two-dimensional acquisition in which the ultrasonic transducer produces a linear or sector acquisition 60 along the compression axis 30, or three-dimensional acquisition, with the ultrasonic transducer 12*b*, which produces a sector or linear array ultrasound data 62, or where an ultrasound beam 60 is swept through an area for a three-dimensional acquisition (not shown) or in acquisitions in which a transducer 12*c* (as shown by ultrasonic transducer 12*c'*) obtains both axial and lateral acquisitions over a three-dimensional or two-dimensional volume. As used herein, "axial" is the direction of the compression axis 30 and the term "lateral" will be used to describe axes that cross the compression axis 30 including, but not necessarily limited to, those perpendicular to the compression axis 30. Thus, the present techniques may apply to a number of elastography applications wherever fine or high resolution displacement must be determined including those techniques described in U.S. patent applications Ser. No. 10/094,844 filed Mar. 8, 2002; U.S. Pat. No. 6,749,571 issued Jun. 15, 2004; Ser. Nos. 10/420,125 filed Apr. 21, 2003; 10/772,663 filed Feb. 4, 2004; 10/765,293 filed Jan. 24, 2005; and 10/784,526 filed Feb. 23, 2005, all hereby incorporated by reference and assigned to the same assignee as the present application.

It should be noted that the present technique can be used with envelope waveforms, transmission ultrasound (as opposed to echo ultrasound), that the sizes of the windows 32 and 54 may be freely adjusted by the user, that this technique can be used in conjunction with other techniques such as stretching of post-compression data and that the image need not be of tissue, but that the present invention is applicable to other materials. It is therefore specifically intended that the present invention not be limited to the embodiments and illustrations contained herein, but include modified forms of those embodiments including portions of the embodiments and combinations of elements of different embodiments as come within the scope of the following claims.

We claim:

1. A method of high-resolution ultrasonic elastography comprising the steps of:
    (a) obtaining a pre-compression and post-compression ultrasonic data set of an imaged object;
    (b) making a first comparison of the pre-compression and post-compression data at a plurality of corresponding first pre-compression regions and first post-compression regions to determine a coarse-displacement of material of the imaged object resulting from compression, the first comparison shifting a given first pre-compression region with respect to at least one first post-compression region to determine the coarse-displacement as a location where the shifting produces greatest correlation;
    (c) using the determined coarse-displacements to identify second post-compression regions smaller than the first post-compression regions and corresponding to a plurality of second pre-compression regions within each first pre-compression region;
    (d) making a second comparison of the pre-compression and post-compression data within the plurality of second pre-compression regions and corresponding second post-compression regions to determine a finer displacement of material of the imaged object resulting from compression, the second comparison shifting a given second pre-compression region with respect to at least one second post-compression region, the at least one second post-compression region identified using the coarse displacement, to determine the fine-displacement as a location where the shifting produces greatest correlation; and
    (e) outputting an elastographic image based on the finer displacement.

2. The method of claim 1 wherein the data of the first pre-compression regions and first post-compression regions are down-sampled to reduce a number of data samples that must be compared.

3. The method of claim 2 wherein the first comparison compares amplitude envelopes of the ultrasonic data sets and the second comparison compares ultrasonic data underlying the amplitude envelopes.

4. The method of claim 1 further comprising after step (d) and before step (e) the steps of:
    (f) using the determined finer-displacements to identify third post-compression regions corresponding to a plurality of third pre-compression regions within each second pre-compression region;
    (g) making a third comparison of the pre-compression and post-compression data within the plurality of third pre-compression regions and corresponding third post-compression regions to determine an even finer displacement of material of the imaged object resulting from compression.

5. The method of claim 4 wherein the data of the first pre-compression regions and first post-compression regions are down-sampled by a first amount to reduce the number of data samples that must be compared, and the data of the second pre-compression regions and first post-compression regions are downsampled by a second amount less than the first amount to reduce a number of data samples that must be compared.

6. The method of claim 4 wherein the first comparison compares amplitude envelopes of the ultrasonic data sets and the second and third comparison compares ultrasonic data underlying the amplitude envelopes.

7. The method of claim 1 wherein the first comparison compares portions of the pre-compression and post-compression ultrasonic data set no less than ten wavelengths.

8. The method of claim 1 wherein the second comparison compares portions of the pre-compression and post-compression ultrasonic data set less than ten wavelengths of ultrasound used to acquire the pre-compression and post-compression ultrasonic data set.

9. The method of claim 8 wherein the second comparison compares portions of the pre-compression and post-compression ultrasonic data set less than two wavelengths of ultrasound used to acquire the pre-compression and post-compression ultrasonic data set.

10. The method of claim 1 wherein the first comparison produces a set of displacement values as a function of depth along an ultrasonic axis through the imaged object and further including the step of interpolating between the set of displacement values to produce the coarse-displacement.

11. The method of claim 1 further including the step of filtering the coarse-displacement before use in step (c).

12. The method of claim 1 wherein pre-compression and post-compression ultrasonic data set are RF data.

13. The method of claim 1 wherein the pre-compression and post-compression ultrasonic data set are ultrasonic signals acquired along an axis of compression.

14. The method of claim 1 wherein the pre-compression and post-compression ultrasonic data set are ultrasonic signals acquired across an axis of compression.

15. The method of claim 1 wherein the first and second comparisons compare two dimensional kernels of the pre-compression and post-compression data.

16. The method of claim 1 wherein first and second comparisons compare three dimensional kernels of the pre-compression and post-compression data.

17. An ultrasonic elastography machine comprising:
    an ultrasonic transducer system for obtaining a pre-compression and post-compression ultrasonic data set of an imaged object;
    an electronic computer receiving the pre-compression and post-compression ultrasonic data set and executing a stored program to:
    (a) make a first comparison of the pre-compression and post-compression data at a plurality of corresponding first pre-compression regions and first post-compression regions to determine a coarse-displacement of material of the imaged object resulting from compression, the first comparison shifting a given first pre-compression region with respect to at least one first post-compression region to determine the coarse-displacement as a location where the shifting produces greatest correlation;

(b) determine coarse-displacements to identify second post-compression regions smaller than the first post compression regions corresponding to a plurality of second pre-compression regions within each first pre-compression region;

(c) make a second comparison of the pre-compression and post-compression data within the plurality of second pre-compression regions and corresponding second post-compression regions to determine a finer-displacement of material of the imaged object resulting from compression, the second comparison shifting a given second pre-compression region with respect to at least one second post-compression region, the at least one second post-compression region identified using the coarse displacement, to determine the fine-displacement as a location where the shifting produces greatest correlation; and (d) output an elastographic image based on the finer displacement.

18. The apparatus of claim 17 wherein the first comparison compares amplitude envelopes of the ultrasonic data sets and the second comparison compares ultrasonic data underlying the amplitude envelopes.

19. The apparatus of claim 17 wherein the stored program, after step and before step (d) executes to:

(e) use the determined finer-displacements to identify locations of third post-compression regions smaller than the second post compression regions and corresponding to a plurality of third pre-compression re within each second pre-compression region;

(f) make a third comparison of the pre-compression and post-compression data within the plurality of third pre-compression regions and corresponding third post-compression regions to determine an even finer displacement of material of the imaged object resulting from compression.

20. The apparatus of claim 19 wherein the first comparison compares amplitude envelopes of the ultrasonic data sets and the second and third comparison compares ultrasonic data underlying the amplitude envelopes.

21. The elastography machine of claim 17 wherein the determination of coarse displacements compares portions of the pre-compression and post-compression ultrasonic data set no less than ten wavelengths.

22. The elastography machine of claim 17 wherein the refining of the determination of coarse displacements compares portions of the pre-compression and post-compression ultrasonic data set less than ten wavelengths of ultrasound used to acquire the pre-compression and post-compression ultrasonic data set.

23. The elastography machine of claim 22 wherein the refining of the coarse determination compares portions of the pre-compression and post-compression ultrasonic data set less than two wavelengths of ultrasound used to acquire the pre-compression and post-compression ultrasonic data set.

24. The elastography machine of claim 17 wherein the determination of coarse displacements first produces a set of displacement values as a function of depth along an ultrasonic axis through the imaged object and second interpolates between the set of displacement values.

25. The elastography machine of claim 17 further including the step of filtering the coarse displacements before its use in refining the coarse determination.

26. The elastography machine of claim 25 wherein the filtration removes data values deviating by more than a predetermined amount from neighboring data values.

* * * * *